United States Patent
Martz et al.

(10) Patent No.: US 12,350,388 B2
(45) Date of Patent: Jul. 8, 2025

(54) METHODS FOR MEASURING AND QUANTIFYING SURFACE CLEANABILITY OF ARTICLES

(71) Applicant: B/E Aerospace, Inc., Winston-Salem, NC (US)

(72) Inventors: Thomas Martz, Winston-Salem, NC (US); Irene Rexwinkle, Mill Creek, WA (US); David C. McConnell, Annalong (GB); Steven Poteet, Ashland, MA (US); Katherine Urena Pimentel, Manchester, CT (US)

(73) Assignee: B/E Aerospace, Inc., Winston-Salem, NC (US)

( * ) Notice: Subject to any disclaimer, the term of this patent is extended or adjusted under 35 U.S.C. 154(b) by 972 days.

(21) Appl. No.: 17/472,188

(22) Filed: Sep. 10, 2021

(65) Prior Publication Data

US 2023/0077611 A1    Mar. 16, 2023

(51) Int. Cl.
*A61L 2/10* (2006.01)
*A61L 2/26* (2006.01)

(52) U.S. Cl.
CPC .. *A61L 2/10* (2013.01); *A61L 2/26* (2013.01)

(58) Field of Classification Search
CPC .................................... A61L 2/10; A61L 2/26
See application file for complete search history.

(56) References Cited

U.S. PATENT DOCUMENTS

| | | |
|---|---|---|
| 2,449,274 A | 9/1948 | Broll |
| 5,143,744 A | 9/1992 | Barth et al. |
| 9,322,760 B2 | 4/2016 | Haberland et al. |

(Continued)

FOREIGN PATENT DOCUMENTS

| | | |
|---|---|---|
| CN | 102507393 A | 6/2012 |
| CN | 104194600 A | 12/2014 |

(Continued)

OTHER PUBLICATIONS

DE 19649925 A1—translation (Year: 1996).*

(Continued)

*Primary Examiner* — Sean E Conley
(74) *Attorney, Agent, or Firm* — Suiter Swantz IP (57) ABSTRACT

Disclosed are methods for quantifying the cleanability of a surface of an article, for instance an aircraft interior component. In embodiments, a solution containing an artificial "dirt" is introduced to a surface under test to simulate a sullied condition. The sullied surface is subjected to at least one cleaning process. Obtained reference and post-cleaning light measurements are compared to determine a measurement difference corresponding to a cleanability of the surface and/or effectiveness of the at least one cleaning process. In embodiments, the measurement difference is assigned a cleanability score for at least one of determining a passing or failing cleanability, modifying the cleaning process, indicating the need for a second or subsequent cleaning, modifying the barrier coating formulation, redesigning the article, etc. The disclosed methods provide solutions for objective verification measures of surface cleanability used to facilitate new article designs, materials, barrier coatings, cleaning processes, cleaners, etc.

10 Claims, 4 Drawing Sheets

(56) References Cited

U.S. PATENT DOCUMENTS

| | | |
|---|---|---|
| 9,587,058 B2 | 3/2017 | Kwon et al. |
| 9,816,909 B2 | 11/2017 | Friedrich et al. |
| 9,861,245 B2 | 1/2018 | Farrugia et al. |
| 9,958,264 B2 | 5/2018 | Williams |
| 10,072,378 B2 | 9/2018 | Baumann |
| 10,196,671 B2 | 2/2019 | Bugler et al. |
| 10,684,232 B2 | 6/2020 | Gordon et al. |
| 10,994,041 B2 | 5/2021 | Wegner et al. |
| 2012/0258244 A1 | 10/2012 | Veerasamy et al. |
| 2014/0186612 A1 | 7/2014 | Kwon et al. |
| 2015/0220867 A1 | 8/2015 | Christensen |
| 2020/0232895 A1 | 7/2020 | Herman et al. |
| 2021/0047673 A1 | 2/2021 | Rovetto et al. |

FOREIGN PATENT DOCUMENTS

| | | |
|---|---|---|
| CN | 106221461 A | 12/2016 |
| CN | 104266940 B | 3/2017 |
| CN | 107603101 A | 1/2018 |
| CN | 107973978 A | 5/2018 |
| CN | 108410295 A | 8/2018 |
| CN | 108648185 A | 10/2018 |
| CN | 110003630 A | 7/2019 |
| CN | 108485353 B | 6/2020 |
| CN | 111363458 A | 7/2020 |
| CN | 112362537 A | 2/2021 |
| CN | 112429974 A | 3/2021 |
| CN | 112552580 A | 3/2021 |
| CN | 110313489 B | 7/2021 |
| DE | 19649925 A1 | 6/1998 |
| DE | 10014584 A1 | 10/2001 |
| DE | 102009058117 A1 | 6/2011 |
| EP | 2657292 B1 | 9/2019 |
| ES | 2215691 | 10/2004 |
| JP | 2003342402 A | 12/2003 |
| KR | 20110077881 A | 7/2011 |
| KR | 101262309 B1 | 5/2013 |
| KR | 101315098 B1 | 10/2013 |
| KR | 101396216 B1 | 5/2014 |
| KR | 101445089 B1 | 9/2014 |
| WO | 2013112207 A1 | 8/2013 |

OTHER PUBLICATIONS

U.S. Appl. No. 17/465,129, filed Sep. 2, 2021, Martz et al.
Anonymous: "Adenosine 5'-triphosphate disodium salt hydrate", 2019, pp. 1-1, XP055982325, Retrieved from the Internet: URL:https://sigmaaldrich.com/content/dam/sigma-aldrich/docs/Sigma/Product_Information_Sheet/a3377pis.pdf [retrieved on Nov. 16, 2022].
Extended European Search Report in European Application No. 22193640.4 dated Nov. 24, 2022, 12 pages.
Quat: Anti-Microbial Clear Coating Against Coronavirus, retrieved from on Sep. 10, 2021, 7 pages.

* cited by examiner

METHODS FOR MEASURING AND QUANTIFYING SURFACE CLEANABILITY OF ARTICLES

TECHNICAL FIELD

The present disclosure relates generally to cleanable articles, and more particularly, to methods for measuring and quantifying the cleanability of a surface of an article using a detectable component introduced to simulate a sullied condition.

BACKGROUND

In response to the coronavirus pandemic, airlines and original equipment manufacturers (OEMs) have focused on improving interior hygiene through the unprecedented use of cleaning products, disinfectants, barrier coatings and ultraviolet (UV) sanitation.

Desirable properties of articles include durability, resistance to fluids, resistance to staining, color fastness, and cleanability. These properties are particularly important in high-traffic interior applications, for instance aircraft passenger cabin environments. These properties can be enhanced through article design, material choice and use of barrier coatings. For example, articles shapes can be optimized for cleanability, materials can be engineered for better performance, and barrier coatings such as siloxane-based coatings can be applied to provide protection against damage from wear, chemicals, exposure to fluids, UV, etc. Coatings and additives can also be used to mitigate the potential spread of infectious agents.

While most articles can be cleaned, at least to a degree, articles in certain environments are subject to constant cleaning using rigorous cleaning processes and harsh chemicals to ensure sanitization. While a degree of cleanability can be assumed from most cleaning processes, there are currently no solutions for measuring and precisely quantifying the cleanability of a surface. Such a solution could be used to ensure sanitization, confirm the effectiveness of a cleaning process, determine the integrity of a barrier coating, and facilitate future designs of articles and barrier coatings, among other purposes.

BRIEF SUMMARY

To achieve the foregoing and other advantages, in a first aspect the present disclosure provides a method for determining cleanability of a surface of an article. In embodiments, the method includes the steps of providing an article having a surface to be cleaned, providing a solution comprising a component measurable in relative light units (RLUs) using an adenosine triphosphate (ATP) bioluminescence meter, applying the solution to the surface of the article, obtaining using the ATP meter a reference ATP bioluminescence measurement of the surface, subjecting the surface of the article having the solution applied thereto to a cleaning process, obtaining using the ATP meter an ATP bioluminescence measurement of the cleaned surface, and quantifying based on a measurement difference between the obtained measurements the cleanability of the surface of the article.

In some embodiments, each of the obtained reference ATP bioluminescence measurement and the quantified measurement difference between the reference ATP bioluminescence measurement and the ATP bioluminescence measurement of the cleaned surface are quantified as a percentage, and wherein the obtained reference ATP bioluminescence measurement corresponds to a 100% sullied surface, a 100% difference between the obtained reference ATP bioluminescence measurement and the obtained ATP bioluminescence measurement of the cleaned surface corresponds to a completely unsullied surface, and less than a 100% difference between the obtained reference ATP bioluminescence measurement and the obtained ATP bioluminescence measurement of the cleaned surface corresponds to a partially sullied surface.

In some embodiments, the percentage difference between the obtained reference ATP bioluminescence measurement and the obtained ATP bioluminescence measurement of the cleaned surface provides a cleanability score, wherein a cleanability score greater than about 50% corresponds to a passing cleanability score, and wherein a cleanability score less than about 50% corresponds to a failing cleanability score.

In some embodiments, the percentage difference between the obtained reference ATP bioluminescence measurement and the obtained ATP bioluminescence measurement of the cleaned surface provides a cleanability score, wherein a cleanability score greater than about 75% corresponds to a passing cleanability score, and wherein a cleanability score less than about 75% corresponds to a failing cleanability score.

In some embodiments, the component in solution is ATP disodium salt.

In some embodiments, the surface of the article, includes a formed barrier coating providing protection against at least one of fluids, disinfectants, chemicals and ultra violet (UV) light.

In some embodiments, the component comprises less than about 75% by volume of the solution, more preferably less than about 50% by volume of the solution.

In some embodiments, the cleaning process includes the steps of applying a cleaning solution to the surface of the article and removing the cleaning solution from the surface of the article, and an optional intermediate wiping step.

In another aspect, the present disclosure, provides a method for determining cleanability of a surface of an article using a fluorescent component. In embodiments, the method includes providing an article having a surface to be cleaned, providing a solution comprising a fluorescent dye excitable using excitation light of a predetermined wavelength range, applying the solution to the surface of the article, obtaining using a fluorescence detector a reference intensity measurement of the surface, subjecting the surface of the article having the solution applied thereto to a cleaning process, obtaining using the fluorescence detector an intensity measurement of the cleaned surface, and quantifying, based on a measurement difference between the obtained reference intensity measurement and the intensity measurement of the cleaned surface, cleanability of the surface of the article.

In some embodiments, each of the obtained reference intensity measurement and the quantified measurement difference between the obtained reference intensity measurement and the intensity measurement of the cleaned surface are quantified as a percentage, wherein the obtained reference intensity measurement corresponds to a 100% sullied surface, a 100% difference between the obtained reference intensity measurement and the obtained intensity measurement of the cleaned surface corresponds to a completely unsullied surface, and less than a 100% difference between the obtained reference intensity measurement and the obtained intensity measurement of the cleaned surface corresponds to a partially sullied surface.

In some embodiments, the percentage difference between the obtained reference intensity measurement and the obtained intensity measurement of the cleaned surface provides a cleanability score, wherein a cleanability score greater than about 50% corresponds to a passing cleanability score, and wherein a cleanability score less than about 50% corresponds to a failing cleanability score.

In some embodiments, the fluorescence detector is configured to excite the surface of the article with excitation light and analyze emitted fluorescent light with a fluorescence monochromator configured to extract predetermined wavelengths and measure intensity using a photomultiplier.

Embodiments of the present disclosure can include or more or any combination of the above features and elements.

This brief summary is provided solely as an introduction to subject matter that is fully described in the detailed description. This brief summary should not be considered to describe essential features nor be used to determine the scope of the claims. Moreover, it is to be understood that both the foregoing summary and the following detailed description are exemplary and explanatory only and are not necessarily restrictive of the subject matter claimed.

BRIEF DESCRIPTION OF THE DRAWINGS

The detailed description is described with reference to the accompanying figures. The use of the same reference numbers in different instances in the description and the figures may indicate similar or identical items. Various embodiments or examples ("examples") of the present disclosure are disclosed in the following detailed description and the accompanying drawings. The drawings are not necessarily to scale. In general, operations of disclosed processes may be performed in an arbitrary order, unless otherwise provided in the claims. In the drawings:

DETAILED DESCRIPTION

Before explaining one or more embodiments of the disclosure in detail, it is to be understood that the embodiments are not limited in their application to the details of construction and the arrangement of the components or steps or methodologies set forth in the following description. In the following detailed description of embodiments, numerous specific details may be set forth to provide a more thorough understanding of the disclosure. However, it will be apparent to one of ordinary skill in the art having the benefit of the instant disclosure that the embodiments disclosed herein may be practiced without some of these specific details. In other instances, well-known features may not be described in detail to avoid unnecessarily complicating the instant disclosure.

Unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of "a" or "an" may be employed to describe elements and components of embodiments disclosed herein. This is done merely for convenience and "a" and "an" are intended to include "one" or "at least one," and the singular also includes the plural unless it is obvious that it is meant otherwise.

Finally, as used herein any reference to "one embodiment" or "some embodiments" means that a particular element, feature, structure, or characteristic described in connection with the embodiment is included in at least one embodiment disclosed herein. The appearances of the phrase "in some embodiments" in various places in the specification are not necessarily all referring to the same embodiment, and embodiments may include one or more of the features expressly described or inherently present herein, or any combination or sub-combination of two or more such features, along with any other features which may not necessarily be expressly described or inherently present in the instant disclosure.

Broadly speaking, the present disclosure provides methods for measuring and quantifying the cleanability of an article, for instance a surface of an aircraft interior component. In a first aspect, an artificial "dirt" is introduced to a surface under test to simulate a sullied condition. The sullied surface is then subjected to at least one cleaning process. Pre-cleaning reference and post-cleaning light measurements obtained using an ATP bioluminescence meter are compared to determine a measurement difference corresponding to the cleanability of the surface. In some embodiments, the measurement difference is assigned a cleanability score used to, for example, determine a passing or failing cleanability, modify the cleaning process, indicate the need for a second or subsequent cleaning, modify the barrier coating formulation, redesign of the article, etc. In a second aspect, a detectable fluorescent indicator is introduced to the surface of the article. The article is then subjected to at least one cleaning process and the measured difference in light intensity pre-cleaning and post-cleaning is used to quantify the cleanability of the surface, the results of which can be used for the purposes discussed above. The methods according to the present disclosure provide solutions for objective verification measures of the cleanability of the surface of an article that can be used to facilitate new article designs, materials, barrier coatings, cleaning processes, cleaners, etc.

Figure 1:
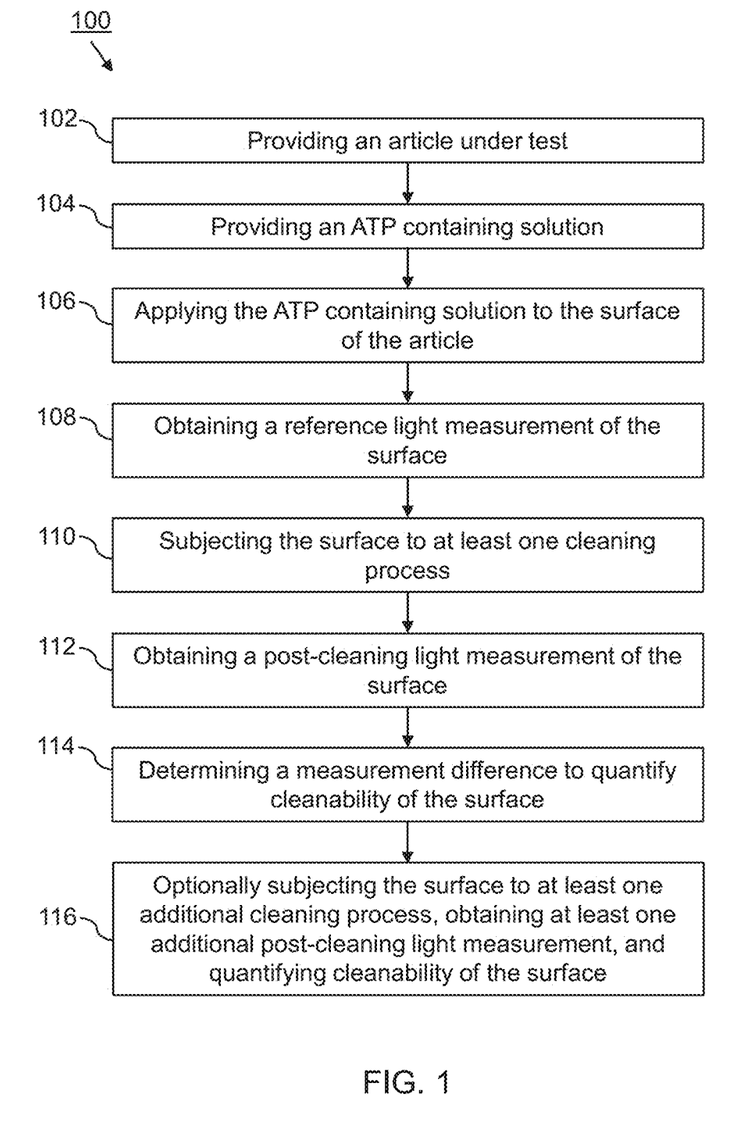
FIG. 1 is a flow diagram of a method for quantifying surface cleanability of an article using an ATP containing solution measurable using an ATP bioluminescence meter, in accordance with one or more embodiments of the present disclosure.

With reference to FIG. 1, a first method 100 according to the present disclosure is used to quantify the cleanability of a surface of an article, for instance a high-contact surface located in a passenger or crew area of a passenger vehicle such as an aircraft, bus, train, ship, etc. Examples of surface materials under test may include, but are not limited to, synthetic or natural fabrics, plastics, metals, composites and composite finishes, wood, glass, leather, etc. Article environments may include, but are not limited to, passenger cabins, crew quarters, lavatories, galleys and cockpits. Other environments may include schools, hospitals, public buildings, etc. In the case of passenger vehicles, the article may be an element of a passenger seat, a passenger suite, an interior panel, an overhead bin, a door, a wall, a passenger amenity, a control panel, a passenger service unit, a lavatory fixture, galley equipment, and beverage carts, among others. In some embodiments, the article may be an element of a mechanism operable for manipulating another element, for example, a handle, lock, latch, switch, control panel or other high-contact surface.

In embodiments, the surface may be coated or uncoated. For example, the surface may be devoid of any protective coating or paint, or may be coated with a single layer or multiple layers of multifunctional barrier coating. In other examples, each coating layer may impart a singular functionality and multiple layers may be registered one atop another to provide a multi-layer coating solution. Coating functionalities may include, but are not limited to, self-cleaning properties, hydrophobicity, fluid resistance, chemical resistance, UV resistance, resistance to wear from physical contact, color fastness, improved flame smoke and toxicity (FST) performance, and antimicrobial properties.

In some embodiments, the barrier coating(s) may be applied via solution, and may include components, individually or in combination, such as base coating components such as siloxanes, silazanes, fluoro-substituted siloxanes or silazanes, polymethylsisequioxane, and polydimethylsiloxane, a binder system including hydrophobic polymer(s) or curable resin(s), a hydrophobic polymer to impart increased water repellency and durability of water repellant as well as resistance to the effects of UV radiation, abrasion and chemical disinfectants, a solvent including tetrahydrofuran for providing uniform coating thickness and rapid drying, as well as good working viscosity, an FST performance enhancing component such as micro- or nano-sized clay particles such as montmorillonite and bentonite functionalized with organosilanes to promote dispersion within the solution, and UV resistant components such as titanium dioxide and triazoles. Different barrier coating formulations may react differently to different cleaning processes based on their components, component volume percentages, layered arrangement, application process, etc., each of which can be optimized utilizing the cleanability measurement methods disclosed herein. Other coating compositions are envisioned and intended.

According to the method 100, in a step 102 an article having a surface under test is provided, for instance an anticipated high-contact surface of an article as discussed above. Also as stated above, the surface may be coated or uncoated and may be any material type. In a step 104, a solution according to the present disclosure is provided. In some embodiments, the solution includes an ATP bioluminescent component, for instance ATP disodium salt or the like. In some embodiments, the ATP is diluted to an amount less than 100% by volume of the solution, more preferably less than about 75% by volume of the solution, and most preferably less than about 50% by volume of the solution.

The ATP containing solution (i.e., the "solution") is formulated to provide a reference relative light unit (RLU) measurement as measured using an ATP bioluminescence meter configured to read the amount of light produced from a surface sample, wherein the light produced is proportional to the amount of ATP. The solution, when applied, introduces an artificial sullied condition to the surface that provides a reference measurement by which cleanability can be quantified. In other words, the ATP solution of a predetermined ATP concentration provides a precise and customizable reference measurement independent of other contaminants that may be present on the surface.

In a step 106, the diluted ATP solution is applied to the surface of the article. In an optional step, the surface may be readied (e.g., cleaned) in one or more cleaning steps prior to step 106 to avoid contamination of the ATP solution. Solution application techniques may include, but are not limited to, spraying, wiping dipping, pouring, etc. The solution may be applied under ambient or controlled conditions and the surface may or may not be subjected to a pre-treatment process prior to solution application. The applied solution may be allowed to dry or cure on the surface. In a step 108, a reference light measurement from the ATP solution is obtained using the ATP bioluminescence meter.

In a step 110, the surface of the article having the solution applied thereto is subjected to at least one cleaning process. The cleaning process may be performed in one or more steps or repetitions of steps. Cleaning may include application of chemicals, disinfectants, solvents, water, etc., via applications such as spraying, wiping, etc. Cleaning processes may also include UV sanitation. Cleaning processes may be singular processes or combinations of different processes, and performed under ambient or controlled conditions. For example, cleaning processes may include conventional techniques using conventional cleaners ordinarily and routinely used for cleaning a predetermined type of article. For example, in the case of a passenger tray table, the cleaning process may include conventional spraying and wiping with a disinfectant cleaner under ambient conditions. Cleaning processes, cleaners, amounts, time durations, etc., may be recorded for use in evaluating cleaning performance.

In a step 112, after the cleaning process is complete, at least one post-cleaning light measurement is obtained using the ATP bioluminescence meter. In a step 114, the post-cleaning light measurement is compared to the reference light measurement to determine a measurement difference indicative of the effectiveness of the cleaning process and/or cleanability of the surface. In some embodiments, the reference light measurement indicates a completely sullied surface, expressed as a percentage such as about 100%, wherein completely is a relative term. The obtained post-cleaning process light measurement is presumably less than 100%, but in some cases may be the same as the reference measurement in situations where the cleaning process is entirely ineffective at removing any amount of ATP. The post-cleaning light measurement obtained, measured for example in RLUs, indicates the amount of ATP remaining on the surface. For example, a 50% reduction in measured light may indicate a 50% reduction in ATP post-cleaning and thus a partially clean surface. In a non-limiting example, a measurement difference of at least 50% may indicate a 'passing' surface cleanability, whereas a measurement difference less than 50% may indicate a 'failing' surface cleanability. Post-cleaning measurements can be taken once after each cleaning process, after each step of a cleaning process, after subsequently performed cleaning processes, etc. Cleanability may be scored other than with measured light corresponding to percentage of dean, and predetermined measurement differences may be selected to determine threshold levels of acceptable surface cleanability. For example, percentages thresholds may include a 100% difference, 75% difference, 50% difference, etc.

For example, the obtained reference light measurement and the difference between the reference light measurement and the post-cleaning light measurement may be expressed as a percentage or otherwise. In the case of percentages, the obtained reference measurement may correspond to a 100% ATP presence on the surface (e.g., dirty), a 100% measurement difference may correspond to a 0% ATP presence on the surface (e.g., dean), and less than a 100% difference may correspond to an amount of ATP remaining on the surface (e.g., partially dean or partially dirty).

Figure 2:
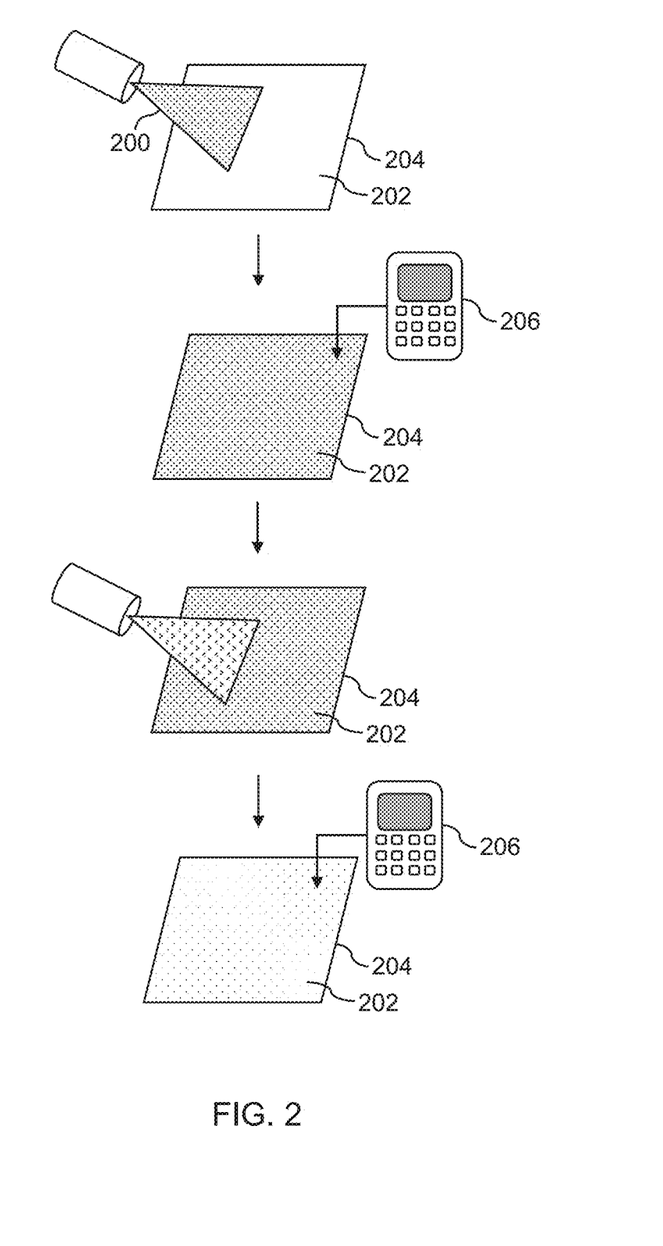
FIG. 2 illustrates schematically the implementation of the method according to FIG. 1.

In an optional step 116, performed after the first light measurement is taken, the article may be subjected to at least one additional cleaning process, and at least one additional post-cleaning light measurement may be taken and compared against the reference light measurement and/or other post-cleaning light measurements. FIG. 2 shows schematically the implementation of the method according to FIG. 1. The ATP solution 200 is applied to the surface 202 of the article 204 and the reference light measurement is obtained using an ATP bioluminescence meter 206. In an alternative embodiment, the light measurement of the reference solution may be a known value. The surface 202 is subjected to at least one cleaning process and at least one post-cleaning light measurement is obtained using the ATP bioluminescence meter 206. The light measurements are then compared to determine the light measurement difference, which can be assigned a score that provides an indication of design/cleaning process capability.

Figure 3:
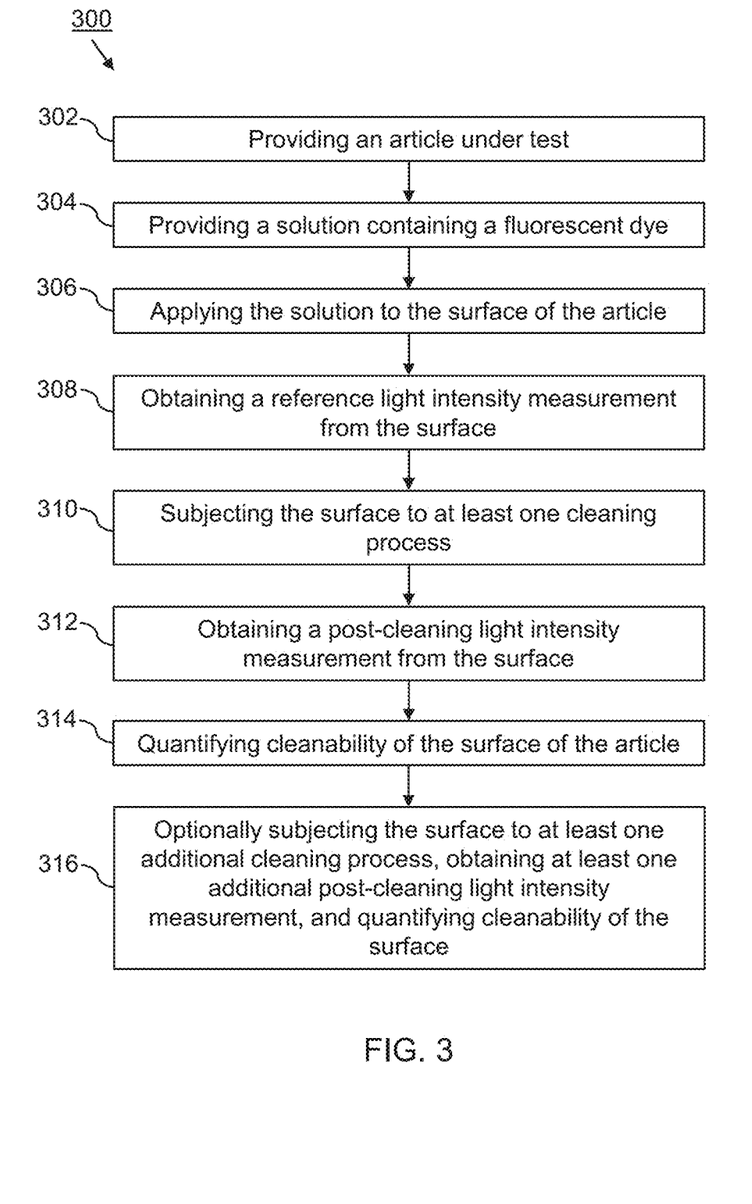
FIG. 3 is a flow diagram of a method for quantifying surface cleanability of an article utilizing a fluorescent dye and fluorescence detector configured to measure intensity, in accordance with one or more embodiments of the present disclosure.

With reference to FIG. 3, another method 300 according to the present disclosure utilizes a fluorescent indicator to determine surface cleanability. Similar to the above method, in a step 302 an article having a surface under test is provided, and in a step 304, a solution including a detectable component is provided, preferably in a diluted amount. In some embodiments, the detectable component is a fluorescent dye. Examples of fluorescent dyes include, but are not limited to, fluorescent indicators such as any fluorescent compound capable of absorption in the UV spectrum and emission in the visible spectrum. For example, the fluorescent compound may absorb radiation in the 100-415 nm wavelength range, more preferably in the 300-415 nm wavelength range, and most preferably in the 365-415 nm wavelength range, and emit radiation in the 100-1000 nm wavelength range, and more preferably emit visible light in the 380-740 nm wavelength range. Suitable fluorescent compounds may be transparent in the presence of visible light and uncolored so as not to alter the color and/or transparency of the surface of the article. Suitable fluorescent compounds can include, but are not limited to, commercially available fluorescent dyes, pigments, colorants and brighteners.

A specific, non-limiting example of a suitable fluorescent compound can include 5-[[4-[bis(2-hydroxyethyl)amino]-6-(4-sulfonatoanilino)-1,3,5-triazin-2-yl]amino]-2-[(E)-2-[4-[[4-[bis(2-hydroxyethyl)amino]-6-(4-sulfonatoanilino)-1,3,5-triazin-2-yl]amino]-2-sulfonatophenyl]ethenyl] benzenesulfonate. Other examples include anionic dye compounds of λex<500 nm and λem>400 nm may be ideally invisible under normal visible light and fluoresce under UV light (e.g., tetrasodium 4,4'-bis[[4-[bis(2-hydroxyethyl)amino]-6-(4-sulphonatoanilino)-1,3,5-triazin-2-yl]amino]stilbene-2,2'-disulphonate], disodium; 5-[[4-anilino-6-[2-hydroxyethyl(methyl)amino]-1,3,5-triazin-2-yl]amino]-2-[2-[4-[[4-anilino-6-[2-hydroxyethyl(methyl)amino]-1,3,5-triazin-2-yl]amino]-2-sulfonatophenyl] ethenyl]benzenesulfonate, disodium 4,4'-bis(4-anilino-6-morpholino-s-triazin-2-ylamino)-2,2'-stilbenedisulfonate, disodium; 54-[4-(2-methylanilino)-6-morpholin-4-yl-1,3,5-triazin-2-yl]amino]-2-[2-[4-[[4-(2-methylanilino)-6-morpholin-4-yl-1,3,5-triazin-2-yl]amino]-2-sulfonatophenyl] ethenyl]benzenesulfonate, hexasodium; 2-[[4-[(3-amino oxopropyl)-(2-hydroxyethyl)amino]-6-[4-[2-[4-[[4-[(3-amino-3-oxopropyl)-(2-hydroxyethyl)amino]-6-(2,5-disulfonatoanilino)-1,3,5-triazin-2-yl]amino]-2-sulfonatophenyl]ethenyl]-3-sulfonatoanilino]-1,3,5-triazin-2-yl]amino] benzene-1,4-disulfonate, and related, as well as fluorescein-SA, Lucifer yellow, sulforhodamine-B or sulforhodamine-101, pyranine, HPTS or HPTS(Lys)3, MPTS, CTR, TSPP, TCPP, PTCA), Dyes (<0.5 wt %), triazine-stilbene, coumarins, imidazolines, diazoles, triazoles, benzoxazoles, and biphenyl stilbenes, individually or in combinations thereof.

In a step 306, the solution is applied to the surface of the article. In an optional step, the surface may be cleaned in one or more cleaning steps prior to step 306 to avoid contamination of the solution affecting light intensity measurement. Solution application techniques may include, but are not limited to, spraying, wiping dipping, and pouring. The solution may be applied under ambient or controlled conditions and the surface may or may not be subjected to a pre-treatment process prior to solution application. The applied solution may be allowed to dry or cure on the surface. In a step 308, a reference light intensity measurement is obtained using, for example, a fluorescence detector configured to excite the fluorescent dye in solution with excitation light of a predetermined wavelength and extract the predetermined fluorescence wavelengths and measure intensity with a photomultiplier.

In a step 310, the surface of the article having the solution applied thereto is subjected to a cleaning process. The cleaning process may be performed in one or more steps or repetitions of steps. Cleaning may include application of chemicals, disinfectants, solvents, water, etc., via applications such as spraying, wiping, etc. Cleaning processes may also include UV sanitation. Cleaning processes may be singular processes or combinations of different processes, and performed under ambient or controlled conditions. For example, cleaning processes may include conventional techniques using conventional cleaners ordinarily and routinely used for cleaning a predetermined type of article. In a specific non-limiting example, the article may be a tray table in an aircraft, and the cleaning process may include conventional spraying and wiping with a disinfectant cleaner. Cleaning processes, amounts, time durations, etc. may be recorded for use in evaluating cleaning performance.

In a step 312, following the at least one cleaning process, at least one post-cleaning light intensity measurement is obtained using the fluorescence detector. In a step 314, the post-cleaning light intensity measurement is compared to the reference light intensity measurement to determine a light intensity difference indicative of the effectiveness of the at least one cleaning process and ultimately the cleanability of the surface. Similar to the above method 100, the reference light intensity measurement can be expressed as a percentage indicating a predetermined sullied condition of the surface. The same applies for the subsequently obtained measurements and measurement differences.

Figure 4:
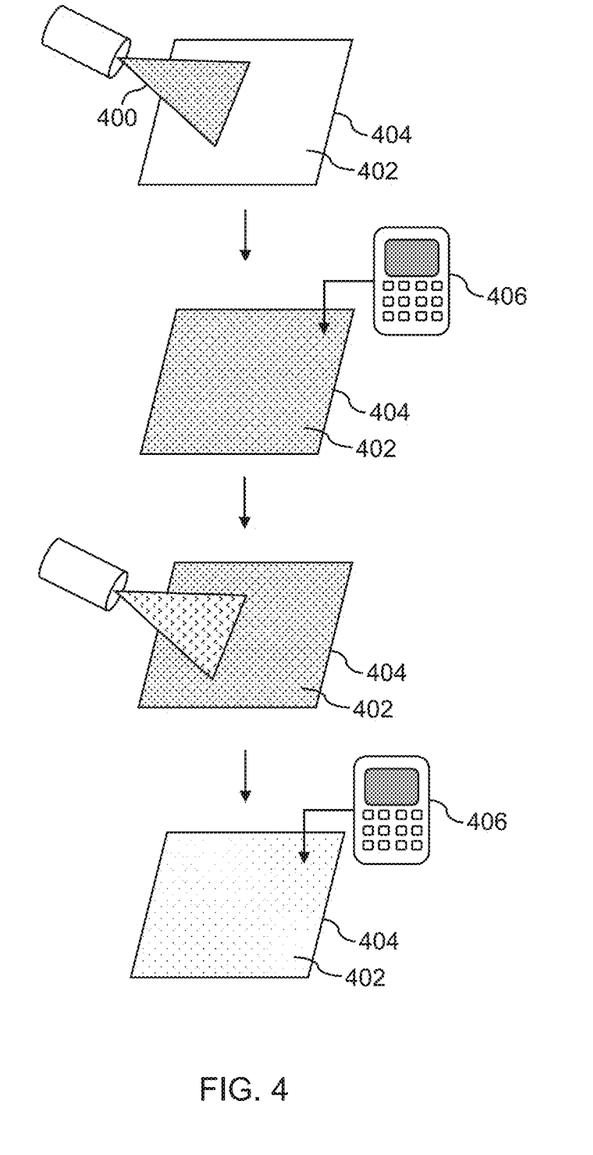
FIG. 4 illustrates schematically the implementation of the method according to FIG. 3.

In an optional step 316, the article may be subjected to at least one additional cleaning process, and at least one additional post-cleaning light intensity measurement may be obtained and compared to the reference light intensity measurement and/or other post-cleaning light intensity measurements. FIG. 4 shows schematically the implementation of the method according to FIG. 4. The solution 400 is applied to the surface 402 of the article 404 and the reference light intensity measurement is obtained. In an alternative embodiment, the light intensity measurement of the solution is a known value. The surface 402 is subjected to at least one cleaning process and at least one post-cleaning light intensity measurement is obtained to determine the measurement difference between the pre- and post-cleaning light intensity measurements. As discussed above, the measurement difference may be assigned a cleanability score indicative of the ability to clean the surface using a predetermined cleaning process.

In some embodiments, a system may include a light source for producing the excitation UV radiation. The light source may be configured to emit radiation in a wavelength, for example, from 300 to 400 nm. For example, the system may include a blacklight. Light generated by the light source may be directed to the surface. The radiation from the light source may interact with the fluorescent indicator in the solution thereby causing the fluorescent indicator to emit light (e.g., visible light in the 400 to 700 nm wavelength range). In some embodiments, the system may be configured to generate an image of the emitted light from the fluorescent indicator. The image of the emitted light from the fluorescent indicator may be generated by a detector, and such detection may occur by analog or digital means. For example, the detector may include, but is not limited to, an ultra-violet (UV) detector, a charge couple device (CCD) detector, a time delay and integration (TDI) detector, a photomultiplier tube (PMT), an avalanche photodiode (APD), a complementary metal-oxide-semiconductor (CMOS) sensor, or the like. The image may have an associated brightness or intensity (e.g., in lumens). The image may also include a color standard. The image may also be a greyscale image.

The system may further include a controller including a memory and a processor, wherein the controller is communicatively coupled with the detector. In this regard, the image generated by the detector may be provided to the controller of the system and stored in the memory. The controller may also process the image to determine an intensity profile. The memory may also include a model for estimating cleanability based on the received reference and post-cleaning images. The model may correlate various data associated with the images (e.g., a luminosity, a brightness, a color standard, etc.) with a cleanability of the surface. The system may be handheld for in field use and may include a power source for powering various components of the system, such as, but not limited to, the controller, detector and the light source. The system may also be configured to image the surface under ambient lighting conditions or under conditions with no ambient lighting.

It is to be understood that embodiments of the methods disclosed herein may include one or more of the steps described herein. Further, such steps may be carried out in any desired order and two or more of the steps may be carried out simultaneously with one another. Two or more of the steps disclosed herein may be combined in a single step, and in some embodiments, one or more of the steps may be carried out as two or more sub-steps. Further, other steps or sub-steps may be carried in addition to, or as substitutes to one or more of the steps disclosed herein.

What is claimed is:

1. A method for determining cleanability of a surface of an article, comprising the steps of:
   providing an article having a surface to be cleaned;
   providing a solution comprising an ATP component, in a diluted amount, measurable in relative light units (RLUs) using an adenosine triphosphate (ATP) bioluminescence meter;
   applying the solution to the surface of the article;
   obtaining, using an ATP bioluminescence meter configured to measure relative RLUs, a reference light measurement of the surface;
   subjecting the surface of the article having the solution applied thereto to a cleaning process;
   obtaining, using the ATP bioluminescence meter, a light measurement of the cleaned surface; and
   quantifying, based on a measurement difference between the obtained reference light measurement and the obtained light measurement of the cleaned surface, cleanability of the surface of the article;
   wherein each of the obtained reference light measurement and the quantified measurement difference between the reference light measurement and the light measurement of the cleaned surface are expressed as a percentage, and wherein the obtained reference light measurement corresponds to a 100% sullied surface, a 100% difference between the obtained reference light measurement and the obtained light measurement of the cleaned surface corresponds to a completely unsullied surface, and less than a 100% difference between the obtained reference light measurement and the obtained light measurement of the cleaned surface corresponds to a partially sullied surface.

2. The method according to claim 1, wherein the percentage difference between the obtained reference light measurement and the obtained light measurement of the cleaned surface corresponds to a surface cleanability score, and wherein a surface cleanability score greater than about 50% corresponds to a passing score.

3. The method according to claim 1, wherein the percentage difference between the obtained reference light measurement and the obtained light measurement of the cleaned surface corresponds to a surface cleanability score, and wherein a surface cleanability score less than about 50% corresponds to a failing score.

4. The method according to claim 1, wherein the percentage difference between the obtained reference light measurement and the obtained light measurement of the cleaned surface corresponds to a surface cleanability score, and wherein a surface cleanability score greater than about 75% corresponds to a passing score.

5. The method according to claim 1, wherein the percentage difference between the obtained reference light measurement and the obtained light measurement of the cleaned surface corresponds to a surface cleanability score, and wherein a surface cleanability score less than about 75% corresponds to a failing score.

6. The method according to claim 1, wherein the ATP component provided in the solution is ATP disodium salt.

7. The method according to claim 1, wherein the surface of the article comprises a barrier coating providing against at least one of fluids, disinfectants, chemicals and ultra violet (UV) light.

8. The method according to claim 1, wherein the ATP component in the solution comprises less than about 75% by volume of the solution.

9. The method according to claim 1, wherein the ATP component in the solution comprises less than about 50% by volume of the solution.

10. The method according to claim 1, wherein the cleaning process comprises the steps of:
    applying a cleaning solution to the surface of the article; and
    removing the cleaning solution from the surface of the article.

* * * * *